(12) United States Patent
Imamura et al.

(10) Patent No.: US 8,097,592 B2
(45) Date of Patent: Jan. 17, 2012

(54) COCRYSTAL OF C-GLYCOSIDE DERIVATIVE AND L-PROLINE

(75) Inventors: Masakazu Imamura, Tokyo (JP); Keita Nakanishi, Tokyo (JP); Ryota Shiraki, Tokyo (JP); Kenichi Onda, Tokyo (JP); Daisuke Sasuga, Tokyo (JP); Masamichi Yuda, Tokyo (JP)

(73) Assignees: Astellas Pharma Inc., Tokyo (JP); Kotobuki Pharmaceutical Co. Ltd., Nagano (JP)

( * ) Notice: Subject to any disclaimer, the term of this patent is extended or adjusted under 35 U.S.C. 154(b) by 464 days.

(21) Appl. No.: 12/296,056

(22) PCT Filed: Apr. 4, 2007

(86) PCT No.: PCT/JP2007/057597
§ 371 (c)(1),
(2), (4) Date: Oct. 3, 2008

(87) PCT Pub. No.: WO2007/114475
PCT Pub. Date: Oct. 11, 2007

(65) Prior Publication Data
US 2009/0143316 A1 Jun. 4, 2009

(30) Foreign Application Priority Data

Apr. 5, 2006 (JP) .................. 2006-103711

(51) Int. Cl.
*A61K 31/70* (2006.01)
*C07H 1/00* (2006.01)
(52) U.S. Cl. ........................ 514/23; 536/1.11
(58) Field of Classification Search ........................ None
See application file for complete search history.

(56) References Cited

U.S. PATENT DOCUMENTS

| 7,202,350 | B2 | 4/2007 | Imamura et al. |
| 2003/0064935 | A1 | 4/2003 | Gougoutas |
| 2006/0122126 | A1 | 6/2006 | Imamura et al. |
| 2007/0161787 | A1 | 7/2007 | Imamura et al. |
| 2008/0004336 | A1 | 1/2008 | Gougoutas et al. |
| 2009/0143316 | A1 | 6/2009 | Imamura et al. |

FOREIGN PATENT DOCUMENTS

| WO | WO 02/083066 A2 | 10/2002 |
| WO | WO 2004/080990 A1 | 9/2004 |
| WO | 2005012326 A1 | 2/2005 |
| WO | WO 2005/023198 A2 | 3/2005 |
| WO | WO 2008/002824 A1 | 1/2008 |
| WO | WO 2008/075736 A1 | 6/2008 |

OTHER PUBLICATIONS

Russian Office Action dated Mar. 25, 2010, as issued in Russian Patent Application No. 2008143362/04(056445).
Rogowska, P. et al., "Evidence for Strong Heterodimeric Interactions of Phenylboronic Acids with Amino Acids," Tetrahedron Letters, vol. 47, No. 9, pp. 1389-1393, (Feb. 2006).
Chinese Office Action dated Sep. 21, 2010 (and English translation), as issued in Chinese Patent Application No. 200780016901.8.
Korean Office Action dated Dec. 28, 2010, as issued in Korean Patent Application No. 10-2008-7027002.
Australian Office Action dated Apr. 8, 2011, as issued in Australian Patent Application No. 2007232763.
Canadian Office Action issued May 27, 2011, in corresponding Canadian Patent Application No. 2,649,022.

*Primary Examiner* — Elli Peselev
(74) *Attorney, Agent, or Firm* — Sughrue Mion, PLLC (57) ABSTRACT

A cocrystal of (1S)-1,5-anhydro-1-[3-(1-benzothien-2-ylmethyl)-4-fluorophenyl]-D-glucitol and L-proline. It is a cocrystal of known compound A, which has a constant quality, is superior in storage stability, has no moisture absorptivity, and is suitable as a crystal of a drug substance used for preparing pharmaceuticals.

6 Claims, 6 Drawing Sheets

COCRYSTAL OF C-GLYCOSIDE DERIVATIVE AND L-PROLINE

CROSS REFERENCE TO RELATED APPLICATIONS

This application is a national phase application of International Application Number PCT/JP2007/057597, filed Apr. 4, 2007, and claims the priority of Japanese Patent Application No. 2006-103711, filed Apr. 5, 2006, the content of both of which is incorporated herein by reference.

TECHNICAL FIELD

The present invention relates to a cocrystal of (1S)-1,5-anhydro-1-[3-(1-benzothien-2-ylmethyl)-4-fluorophenyl]-D-glucitol (hereinafter referred to from time to time as "C-glycoside derivative A" or simply "known compound A") and L-proline. More particularly, the present invention relates to a cocrystal of C-glycoside derivative A and L-proline, which has a constant quality and is superior in storage stability, as a crystal of a drug substance used for preparing pharmaceuticals, as well as to a pharmaceutical composition containing the cocrystal as an effective ingredient, which is useful particularly as a diabetes treating agent.

BACKGROUND ART

The inventors of the present invention reported that (1S)-1,5-anhydro-1-[3-(1-benzothien-2-ylmethyl)-4-fluorophenyl]-D-glucitol (known compound A) represented by the following chemical formula is a useful compound as a $Na^+$-glucose cotransporter inhibitor, for treating and preventing of diabetes, such as insulin-dependent diabetes (type 1 diabetes) and noninsulin-dependent diabetes (type 2 diabetes), insulin resistance diseases, and obesity (Patent Document 1, see Example 138).

[Chemical formula 1]

Patent Document 1: WO2004/080990

DISCLOSURE OF THE INVENTION

It was found that the crystal of known compound A disclosed in the Patent Document 1 forms a clathrate hydrate and changes reversibly from an anhydrous compound to a non-stoichiometric hydrate depending on hygrothermal condition. Therefore, it was found that known compound A is unable to retain a constant quality as a drug substance used for preparing pharmaceuticals.

Hence, the inventors of the present invention made a study on the crystallization conditions for obtaining a crystal of known compound A which forms no clathrate hydrate. Specifically explaining, the inventors of the present invention made a study on such crystallization conditions by dissolving known compound A, with heating, in a single solvent selected from methanol, ethanol, 2-propanol, dimethylformamide, tetrahydrofuran, acetone, methyl ethyl ketone, ethyl acetate, acetic acid, pyridine, 1,4-dioxane, acetonitrile, anisole, water, toluene, diethyl ether, diisopropyl ether, di-n-butyl ether, n-hexane, cyclohexane, n-heptane, chloroform and carbon tetrachloride, or in a mixed solvent which were a combination of two kinds or more of the above single solvents and then cooling the resulting solution slowly.

As a result of the above study, there were obtained, in most of the crystallization conditions, a crystal which forms a clathrate hydrate and, in part of the crystallization conditions, only a crystal solvated with part or the whole of the crystallization solvent used. Any solvated crystal containing a solvent, which causes a safety problem, in a large amount is unsuitable as a drug substance to be used in pharmaceuticals. Therefore, there was a problem that use of known compound A of free form, as a drug substance in production of drugs is impossible practically.

Further, known compound A is present as a non-ionic compound in an ordinary pH range. Therefore, it was impossible to avoid the above problem by forming a pharmaceutically acceptable salt of known compound A.

The present invention has been achieved in order to solve the above problems. The present invention has an object of providing a cocrystal of known compound A, which has a constant quality, is superior in storage stability and is suitable as a crystal of a drug substance used for preparing pharmaceuticals.

In order to achieve the above-mentioned object, the inventors of the present invention made a study on the formation of a cocrystal of known compound A and an amino acid. As a result, no cocrystal could be obtained between known compound A and any of glycine, L-asparagine, L-aspartic acid, L-glutamine, L-glutamic acid, L-lysine, L-arginine, L-histidine, L-serine, L-threonine, L-cysteine, L-methionine, L-phenylalanine, L-tyrosine, L-tryptophan, L-alanine, L-valine, L-leusine, L-isoleusine, D-asparagine, D-aspartic acid, D-glutamine, D-glutamic acid, D-arginine, D-serine, D-threonine, D-methionine, D-phenylalanine, D-alanine, D-valine, D-leusine, D-isoleusine and D-proline.

On the other hand, it was found that known compound A and L-proline form, at a 1:1 molar ratio, a single cocrystal of constant quality at good reproducibility. It was also found that the cocrystal is superior in storage stability and can be supplied stably as a crystal of a drug substance used for preparing pharmaceuticals. The findings have led to the completion of the present invention.

In order to achieve the above-mentioned object, the following cocrystal of C-glycoside derivative A and L-proline (the cocrystal is hereinafter referred to from time to time as "a cocrystal of the present invention") and a pharmaceutical composition containing the cocrystal as an effective ingredient, which is particularly suitable as a diabetes treating agent are provided according to the present invention.

[1] A cocrystal of (1S)-1,5-anhydro-1-[3-(1-benzothien-2-ylmethyl)-4-fluorophenyl]-D-glucitol and L-proline.

[2] The cocrystal according to [1], wherein the molar ratio of (1S)-1,5-anhydro-1-[3-(1-benzothien-2-ylmethyl)-4-fluorophenyl]-D-glucitol and L-proline is 1:1.

[3] The cocrystal according to [1], having an endothermic peak at 201 to 213° C. measured by differential scanning calorimetry (DSC analysis).

[4] The cocrystal according to [1], having peaks at 2θ (°) of 4.14, 8.98, 12.4, 16.5, 17.5, 18.7, 20.5 and 21.5 measured by X-ray powder diffraction.

[5] The cocrystal according to [1], having an endothermic peak at 201 to 213° C. measured by differential scanning calorimetry (DSC analysis) and peaks at 2θ (°) of 4.14, 8.98, 12.4, 16.5, 17.5, 18.7, 20.5 and 21.5 measured by X-ray powder diffraction.

[6] A pharmaceutical composition comprising the cocrystal according to any one of [1] to [5] as an effective ingredient.
[7] A pharmaceutical composition produced using the cocrystal according to any one of [1] to [5].
[8] The pharmaceutical composition according to [6] or [7], further comprising a pharmaceutically acceptable excipient.
[9] The pharmaceutical composition according to any one of [6] to [8], which is a diabetes treating agent.
[10] Use of a cocrystal according to any one of [1] to [5], in production of a diabetes treating agent.
[11] A method for treating of diabetes comprising administering an effective therapeutic dose of the cocrystal according to any one of [1] to [5] to patients.

According to the present invention, there are provided a cocrystal of known compound A and L-proline, which has a constant quality and is superior in storage stability as a crystal of a drug substance used for preparing pharmaceuticals, and a pharmaceutical composition containing the cocrystal as an effective ingredient, which is particularly suitable as a diabetes treating agent.

BEST MODE FOR CARRYING OUT THE INVENTION

The best mode for carrying out the present invention will be described below specifically. A cocrystal of the present invention of C-glycoside derivative A ((1S)-1,5-anhydro-1-[3-(1-benzothien-2-ylmethyl)-4-fluorophenyl]-D-glucitol) and L-proline has a chemical structure shown below.

[Chemical formula 2]

As mentioned above, differing from the crystal which forms a clatherate hydrate, the cocrystal of the present invention is obtained as a cocrystal having a constant quality, at good reproducibility, can be supplied stably as a crystal of a drug substance used for preparing pharmaceuticals, and is superior in storage stability. The difference of crystal form between known compound A which forms a clatherate hydrate and the cocrystal of the present invention is clear particularly from the results of differential scanning calorimetry analyses (DSC analyses) and X-ray powder diffraction.

Specifically, the cocrystal of the present invention has an endothermic peak at 201 to 213° C. measured by differential scanning calorimetry analysis (DSC analysis) and/or has peaks about 2θ (°) of 4.14, 8.98, 12.4, 16.5, 17.5, 18.7, 20.5 and 21.5 measured by X-ray powder diffraction.

Known compound A is characterized by the diffraction angles (2θ (°)) and the relative intensity measured by X-ray powder diffraction, shown in Table 1. On the other hand, the cocrystal of the present invention is characterized by the diffraction angles (2θ (°)) and relative intensity measured by X-ray powder diffraction, shown in Table 2. Incidentally, due to the nature of the data obtained by the X-ray powder diffraction, the crystal lattice interval and overall pattern are important in identifying crystals, and the relative intensity, which more or less varies according to the direction of crystal growth, the size of particles, and measuring conditions, should not strictly be construed.

TABLE 1

| Diffraction angle | Relative intensity |
|---|---|
| 9.80 | Medium |
| 11.9 | Medium |
| 15.4 | Medium |
| 18.8 | Strong |
| 20.1 | Strong |
| 23.9 | Strong |

In the crystal (known compound A), which forms a clatherate hydrate, there is seen a phenomenon that, when the crystal has formed a non-stoichiometric hydrate, a change arises in the facing of crystal and resultantly a shift in diffraction angle arises.

TABLE 2

| Diffraction angle | Relative intensity |
| --- | --- |
| 4.14 | Medium |
| 8.98 | Medium |
| 12.4 | Medium |
| 16.5 | Medium |
| 17.5 | Strong |
| 18.7 | Strong |
| 20.5 | Strong |
| 21.5 | Medium |

"X-ray powder diffraction" and "differential scanning calorimetric analysis (DSC analysis)" were conducted under the following conditions.
(X-Ray Powder Diffraction)
(1) Standard Measurement
"MAC Science MXP18TAHF22" equipped with a copper X-ray tube was used under the conditions of a current of 200 mA, a tube voltage of 40 kV, a sampling width of 0.020°, a scanning rate of 3'/min, wavelength of 1.54056 Å, and measurement angles of diffraction range of (2θ): 3 to 40°.
(2) Humidity-Controlled Measurement
"MAC Science MXP 18 TAHF 22 with a multifunctional humidity and temperature converter (VAISALA MHP 235)" equipped with a copper X-ray tube was used under the conditions of a current of 350 mA, a tube voltage of 50 kV, a sampling width of 0.020°, a scanning rate of 3°/min, wavelength of 1.54056 Å, and measurement angles of diffraction range of (2θ): 5 to 40°.
(Differential Scanning Calorimetric Analysis (DSC Analysis))
"TA Instrument TA 5000" was used at a temperature from room temperature to 300° C. (10° C./min) and a $N_2$ feed rate of 50 mL/min using an aluminum sampling pan.
(Method of Preparation)
The cocrystal of the present invention can be prepared by using the free-form of C-glycoside derivative A described in Example 138 of Patent Document 1 and L-proline, as shown in the following formula. That is, (1S)-1,5-anhydro-1-[3-(1-benzothien-2-ylmethyl)-4-fluorophenyl]-D-glucitol (known compound A) and L-proline are stirred at a molar ratio of about 1:1 with heating in an appropriate solvent. After the reaction mixture is slowly cooled with stirring, the resulting solid is collected by filtration. The solid washed with an appropriate solvent is dried, and then subjected to recrystallization using an appropriate solvent. The resulting crystal is collected by filtration, washed with an appropriate solvent, and dried, whereby can be obtained the cocrystal (cocrystal of the present invention) of (1S)-1,5-anhydro-1-[3-(1-benzothien-2-ylmethyl)-4-fluorophenyl]-D-glucitol and L-proline.

[Chemical formula 3]

Known compound A

L-proline

Cocrystal of the present invention

As specific examples of the solvent, there can be mentioned alcohols (e.g. methanol, ethanol, 2-propanol and n-propanol), water, and mixed solvents thereof. The temperature of stirring with heating is ordinarily about 40 to 150° C., preferably about 60 to 100° C. The time of stirring with heating is ordinarily about 15 minutes to 2 hours, preferably about 20 minutes to 1 hour. The temperature of stirring with cooling is ordinarily about −20 to 20° C., preferably about 0 to 10° C. The time of stirring with cooling is ordinarily about 30 minutes to 3 hours, preferably about 1 to 2 hours. The drying is conducted ordinarily under vacuum-heating. The temperature of drying is ordinarily about 30 to 100° C., preferably about 40 to 60° C.

The cocrystal of the present invention obtained by above-mentioned method is obtained by using C-glycoside derivative A and L-proline at a molar ratio of about 1:1. Therefore, the cocrystal of the present invention is considered to be ordinarily a 1:1 (molar ratio) cocrystal of C-glycoside derivative A and L-proline.

The pharmaceutical composition of the present invention contains the above-mentioned cocrystal of the present invention as an effective ingredient. Also, the pharmaceutical composition of the present invention is prepared by using the above-mentioned cocrystal of the present invention. The pharmaceutical composition of the present invention may further comprise a pharmaceutically acceptable excipient as a component other than the cocrystal of the present invention. And the pharmaceutical composition of the present invention is particularly useful as a diabetes treating agent.

The pharmaceutical composition containing the cocrystal of the present invention as an effective ingredient can be formed into tablets, powders, subtle granules, granules, capsules, pills, liquid preparations, injections, suppositories, ointments, pasting agents, and the like, using excipients, vehicles, and other additives which are commonly used for preparing pharmaceuticals. These preparations are administered orally or non-orally.

Although a clinical dose (effective dose for remedy) of the cocrystal of the invention for a human is appropriately determined taking into consideration the symptoms, weight, age, sex, and the like of the patient to whom the pharmaceutical is administered, a daily dose to an adult is usually 0.1 to 500 mg per-oral and 0.01 to 100 mg per-nonoral administration. These doses are prescribed to the patient at one time or over several applications. Since a dose can change according to various conditions, a dose smaller than the above range is sufficient in some cases.

A tablet, a powder, a granule, and the like are used as a solid composition of cocrystal of the invention for oral administration. In such a solid composition, one or more active compounds are mixed with at least one inert diluent such as lactose, mannitol, glucose, hydroxypropyl cellulose, microcrystalline cellulose, starch, polyvinylpyrrolidone, and magnesium aluminometasilicate. According to a common practice, the composition may contain additives other than the inert diluent. For example, a lubricant such as magnesium stearate, a disintegrator such as cellulose calcium glycolic acid, a stabilizer such as lactose, and a solubilizing agent or a solubilizing adjuvant such as glutamic acid or aspartic acid may be added. As required, the tablets or pills may be provided with a sugar coating such as a coating of sucrose, gelatin, hydroxypropyl cellulose, or hydroxypropyl methylcellulose phthalate, or a film of an enteric or stomach soluble substance.

The liquid composition for oral administration contains a pharmaceutically acceptable emulsifier, solution agent, suspending agent, syrup, elixir, and the like, as well as a common inert diluent such as purified water and ethyl alcohol. In addition to the inert diluents, the composition may contain an assisting agent such as a solubilizing agent, a solubilizing adjuvant, a wetting agent, and a suspending agent, as well as a sweetener, a flavor agent, a perfume, and an antiseptic agent.

The injection preparation to be nonorally administered contains a sterile aqueous or non-aqueous solution agent, a suspending agent, and an emulsifier. As examples of the aqueous solution agent and aqueous diluent of a suspending agent, distilled water for injection and a physiological saline solution can be given. As examples of a non-aqueous solution agent and non-aqueous diluent of a suspending agent, vegetable oils such as propylene glycol, polyethylene glycol, and olive oil; alcohols such as ethyl alcohol; and Polysolvate 80 (commercial name) can be given.

The composition may further contain other additives such as an isotonic agent, an antiseptic agent, a wetting agent, an emulsifier, a dispersant, a stabilizer (for example, lactose), a solubilizing agent, and a solubilizing adjuvant. These additives are sterilized by filtration through a bacteria suspension filter, addition of a disinfectant, or irradiation. A sterile solid composition may be prepared from these additives and dissolved in aseptic water or a sterile solvent for injection prior to use.

EXAMPLES

The present invention will be described in more detail by examples which are not intended to be limiting of the present invention.

Reference Example 1

Figure 1:
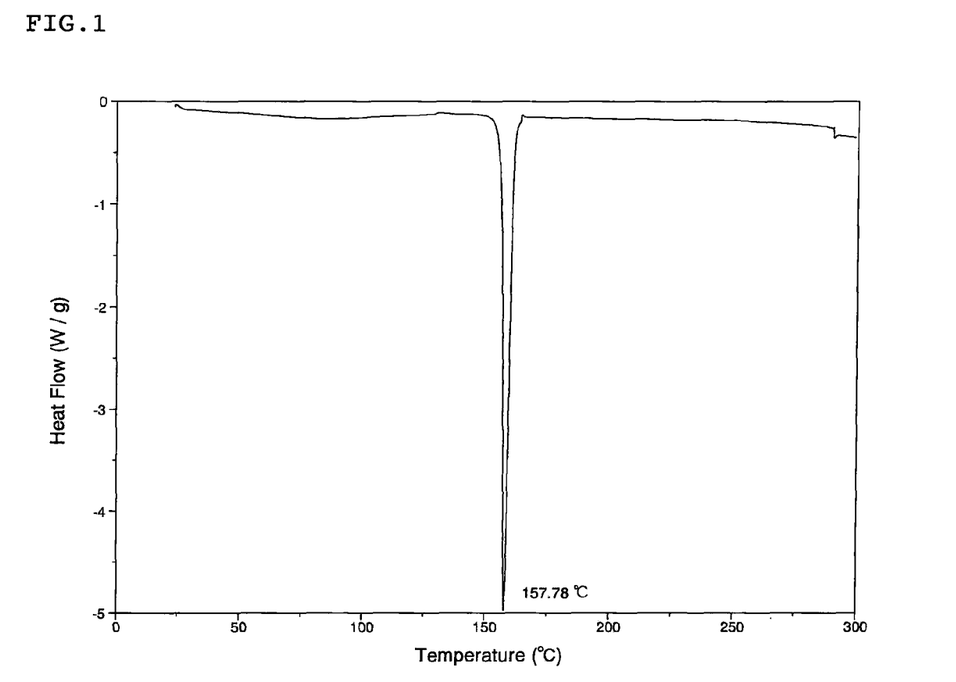
FIG. 1 is a differential scanning calorimetry analysis chart (DSC analysis chart) of (1S)-1,5-anhydro-1-[3-(1-benzothien-2-ylmethyl)-4-fluorophenyl]-D-glucitol (known compound A).
Figure 2:
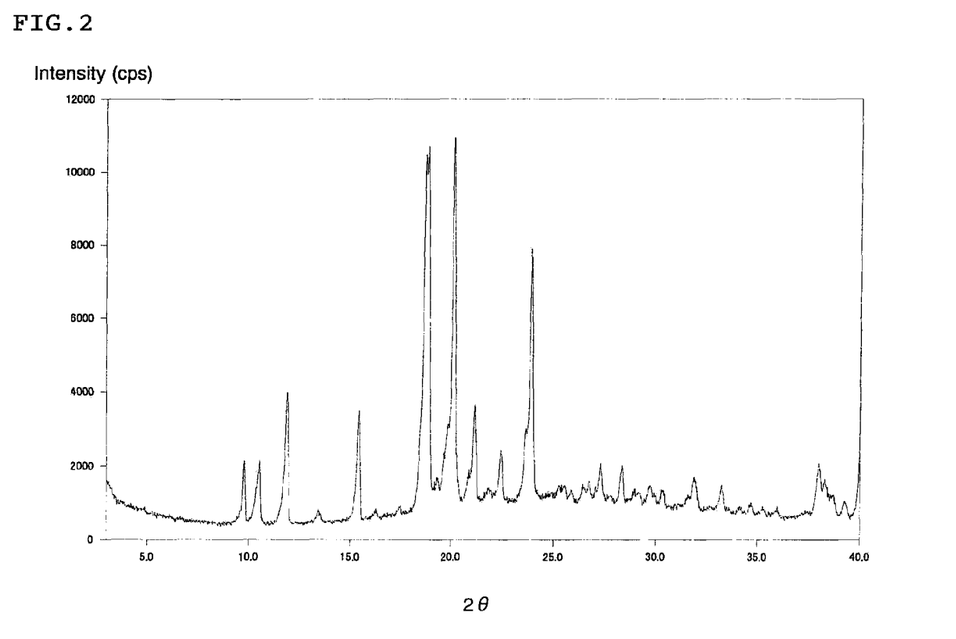
FIG. 2 is an X-ray powder diffraction chart of (1S)-1,5-anhydro-1-[3-(1-benzothien-2-ylmethyl)-4-fluorophenyl]-D-glucitol (known compound A).

Pentamethylbenzene (4.85 g) and a n-heptane solution (16.3 mL) containing 1.0 M of boron trichloride were added to a solution of (1s)-1,5-anhydro-1-[3-(1-benzothien-2-ylmethyl)-4-fluorophenyl]-2,3,4,6-tetra-O-benzyl-D-glucitol (2.5 g) dissolved in dichloromethane (50 mL, cooled to −78° C.) in an argon stream. The mixture was stirred at the same temperature for 2 hours. After the completion of the reaction, methanol (100 mL) was added for decomposition of the excessive reagent, and the solvents were removed by vacuum distillation. The residue was purified by silica gel column chromatography (chloroform-methanol). The obtained residue was suspended in a mixed solvent of ethanol and water and was refluxed with heating to dissolve. The resulting solution was slowly cooled to room temperature for recrystallization. The obtained crystal was collected by filtration and then dried under vacuum and heating to obtain (1S)-1,5-anhydro-1-[3-(1-benzothien-2-ylmethyl)-4-fluorophenyl]-D-glucitol (known compound A) (1.1 g) as a white crystal. The differential scanning calorimetry analysis chart (DSC analysis chart) of the known compound A obtained is shown in FIG. 1, and its X-ray powder diffraction chart is shown in FIG. 2.

Reference Example 2

Figure 3:
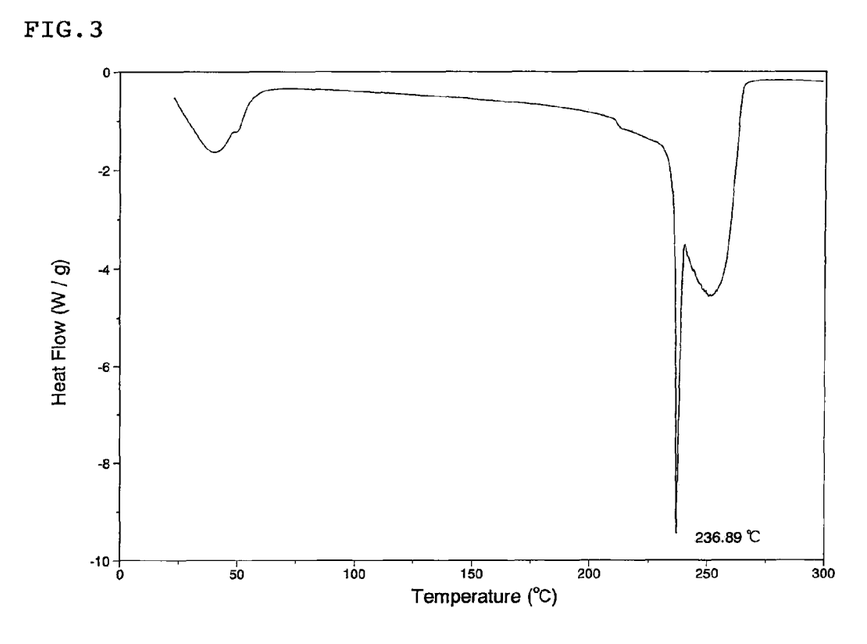
FIG. 3 is a differential scanning calorimetry analysis chart (DSC analysis chart) of L-proline.
Figure 4:
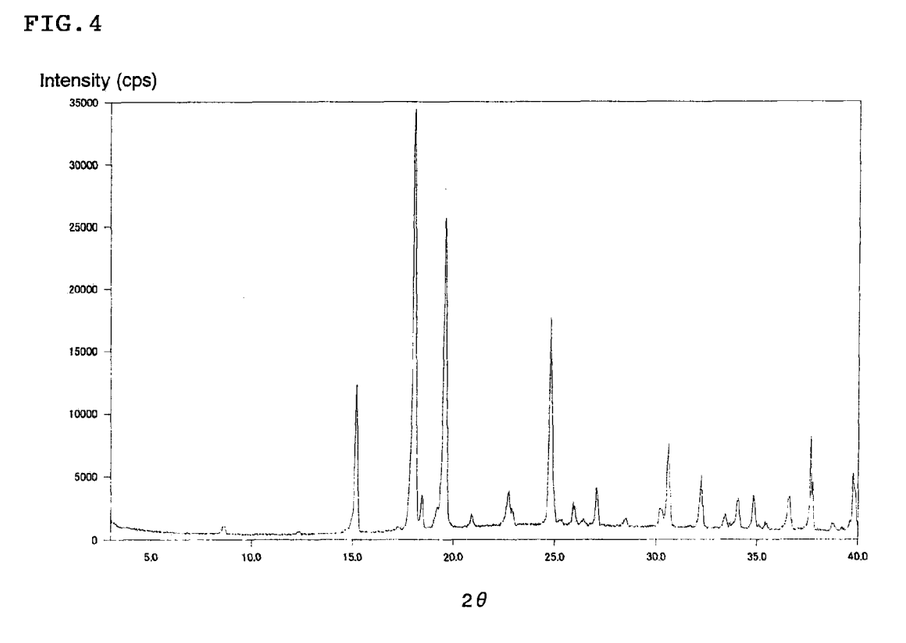
FIG. 4 is an X-ray powder diffraction chart of L-proline.

The differential scanning calorimetry analysis chart (DSC analysis chart) of L-proline is shown in FIG. 3, and its X-ray powder diffraction chart is shown in FIG. 4.

Example 1

Figure 5:
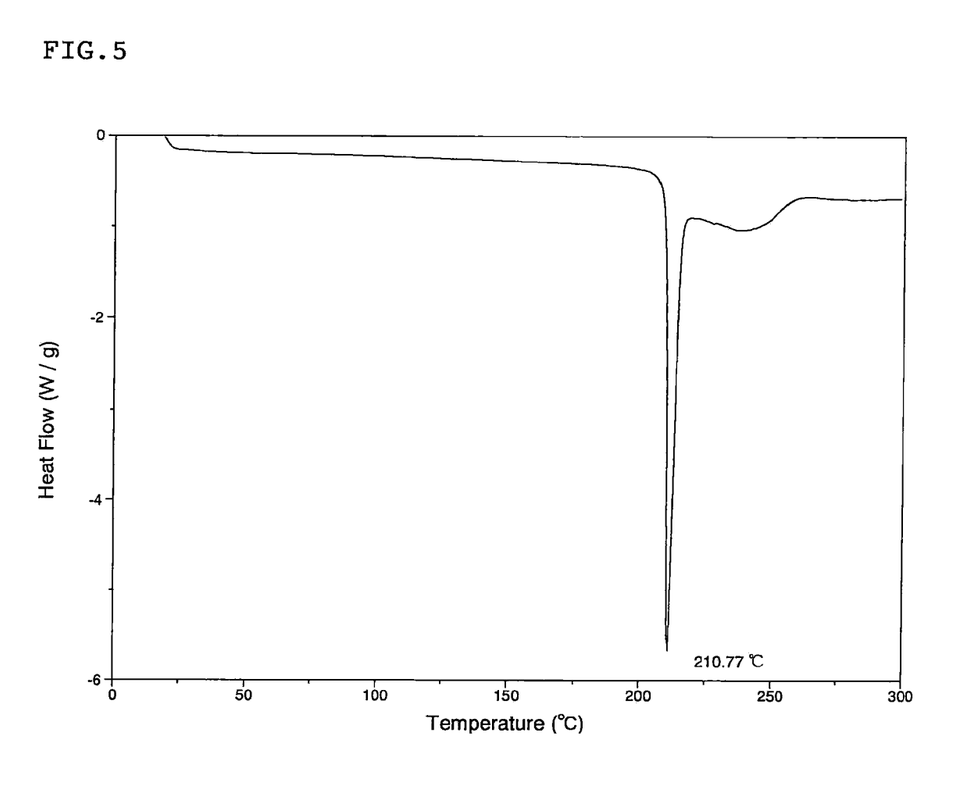
FIG. 5 is a differential scanning calorimetry analysis chart (DSC analysis chart) of a cocrystal (a cocrystal of the present invention) of (1S)-1,5-anhydro-1-[3-(1-benzothien-2-ylmethyl)-4-fluorophenyl]-D-glucitol and L-proline.
Figure 6:
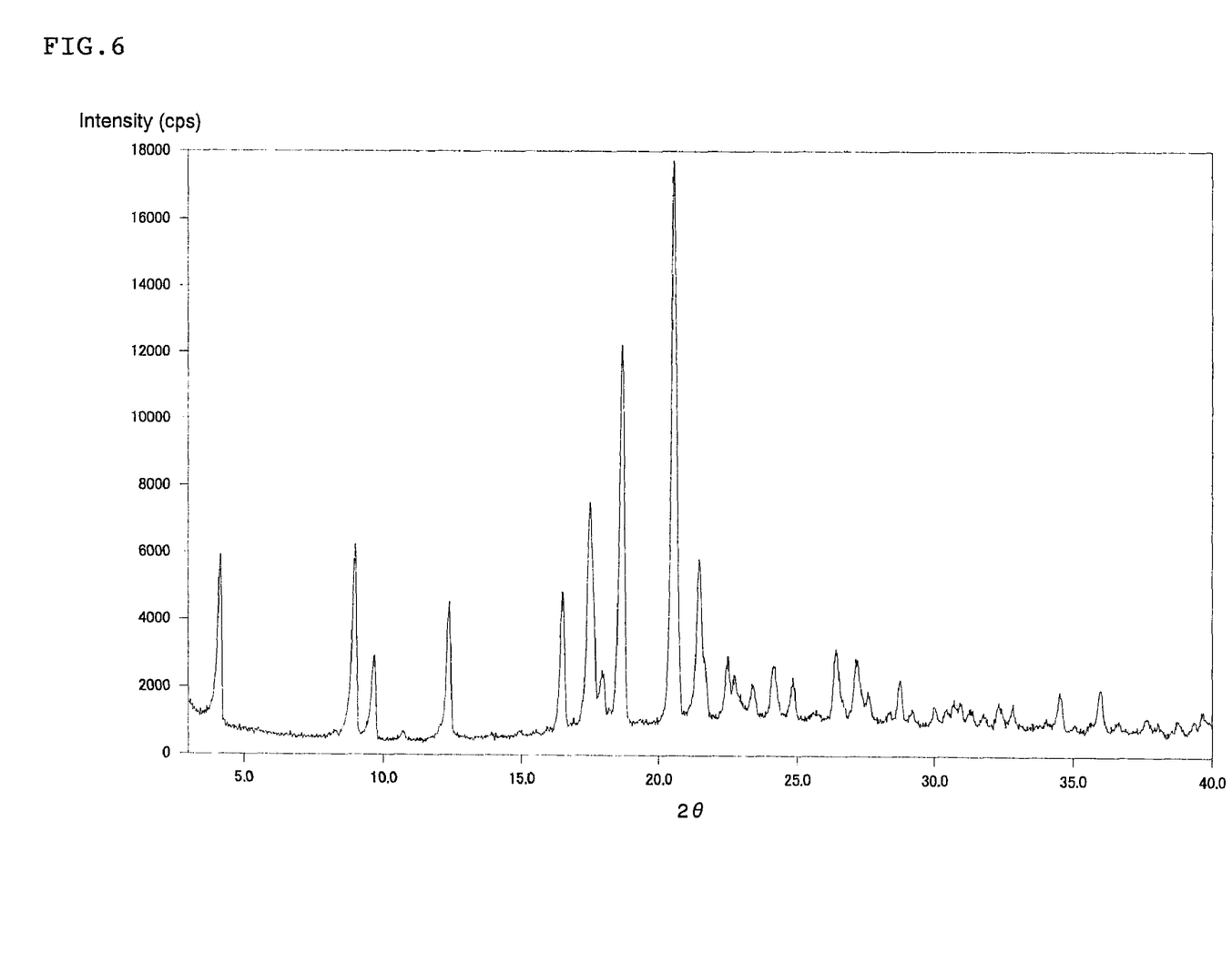
FIG. 6 is an X-ray powder diffraction chart of a cocrystal (a cocrystal of the present invention) of (1S)-1,5-anhydro-1-[3-(1-benzothien-2-ylmethyl)-4-fluorophenyl]-D-glucitol and L-proline.

L-proline (570 mg) was added to an ethanol (25 mL) suspension of (1S)-1,5-anhydro-1-[3-(1-benzothien-2-ylmethyl)-4-fluorophenyl]-D-glucitol (known compound A) (2.0 g). The reaction mixture was stirred at 100° C. for 30 minutes. After the reaction mixture was slowly cooled to room temperature, the resulting solid was collected by filtration and washed with ethanol. The obtained solid was dried under vacuum and heating, and the solid was suspended in a mixed solvent of ethanol and water. The suspension was refluxed with heating for dissolution. The resulting solution was slowly cooled and stirred for 1 hour with ice-cooling. The resulting crystal was collected by filtration, washed with ethanol, and dried under vacuum and heating to obtain a cocrystal (the cocrystal of the present invention) (1.7 g) of (1S)-1,5-anhydro-1-[3-(1-benzothien-2-ylmethyl)-4-fluorophenyl]-D-glucitol and L-proline. The differential scanning calorimetry analysis chart (DSC analysis chart) of the obtained cocrystal of the present invention is shown in FIG. 5, and its X-ray powder diffraction chart is shown in FIG. 6.

As shown in the profiles of the differential scanning calorimetry analysis charts (DSC analysis charts) and X-ray powder diffraction charts of FIGS. 1 to 6, it is considered that the cocrystal of known compound A and L-proline was obtained in Example 1, and not a mere mixture of known compound A and L-proline.

Industrial Applicability

Since the cocrystal of the present invention of (1S)-1,5-anhydro-1-[3-(1-benzothien-2-ylmethyl)-4-fluorophenyl]-D-glucitol and L-proline have excellent storage stability and exhibit $Na^+$-glucose cotransporter-inhibiting and antihyperglycemic action, the cocrystal is useful as a pharmaceutical, particularly as a $Na^+$-glucose cotransporter inhibitor, for treating and preventing diabetes, such as insulin-dependent diabetes mellitus (type 1 diabetes) and noninsulin-dependent diabetes mellitus (type 2 diabetes), insulin resistance diseases, and obesity.

The excellent storage stability, and the superior Human $Na^+$-glucose cotransporter-inhibiting action and antihyperglycemic action of the cocrystal of the present invention have been confirmed by [Storage stability test], [Moisture absorptivity test], and [Pharmacological tests] (Test 1 and Test 2) shown below.

[Storage Stability Test]

Figure 7:
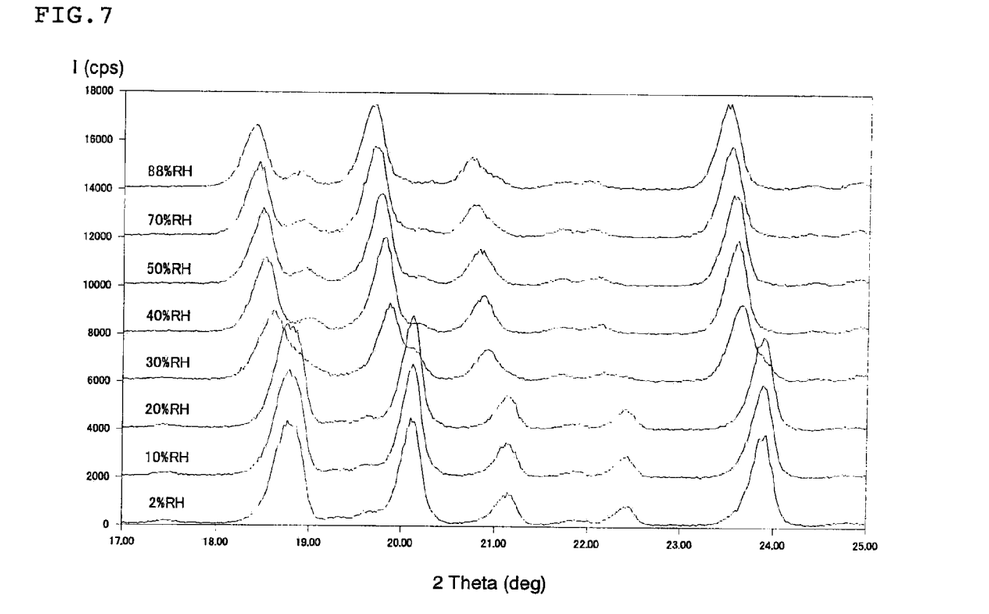
FIG. 7 is an X-ray powder diffraction chart of (1S)-1,5-anhydro-1-[3-(1-benzothien-2-ylmethyl)-4-fluorophenyl]-D-glucitol (known compound A), obtained by measurements at various humidities.

The measurement of X-ray powder diffraction was conducted continuously at 25° C. in a relative humidity range of 2 to 88%. As a result, known compound A was confirmed to show shift of diffraction angle, associated with the change of relative humidity (see FIG. 7). Further, its crystals each of free form, obtained from various crystallization conditions were physically unstable crystals having a feature of reversibly forming a non-stoichiometric clathrate hydrate at room temperature and a low humidity.

Figure 8:
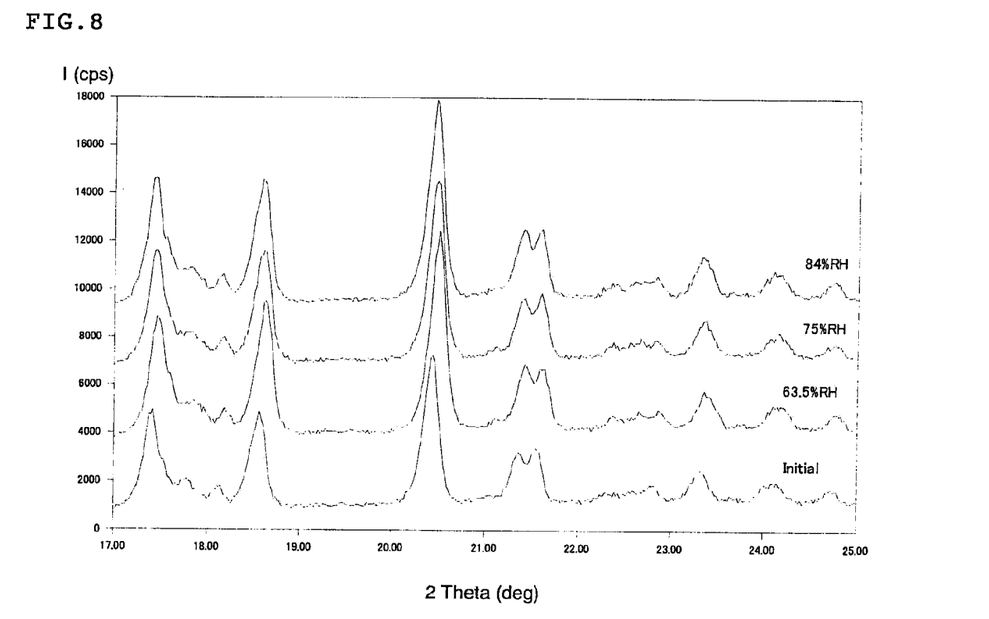
FIG. 8 is an X-ray powder diffraction chart of a cocrystal (a cocrystal of the present invention) of (1S)-1,5-anhydro-1-[3-(1-benzothien-2-ylmethyl)-4-fluorophenyl]-D-glucitol and L-proline, which was stored for 7 days at various humidities, as compared with an X-ray diffraction graph of the same cocrystal before storage.

In contrast, the cocrystal of the present invention showed no physical change when allowed to stand up to 7 days at room temperature (25° C.) at 63.5% RH to 84% RH (see FIG. 8). Further, the cocrystal was physically stable for at least two months even when allowed to stand at 40° C./75% RH/open, 60° C./uncontrolled humidity or 80° C./uncontrolled humidity.

[Moisture Absorptivity Test]

Figure 9:
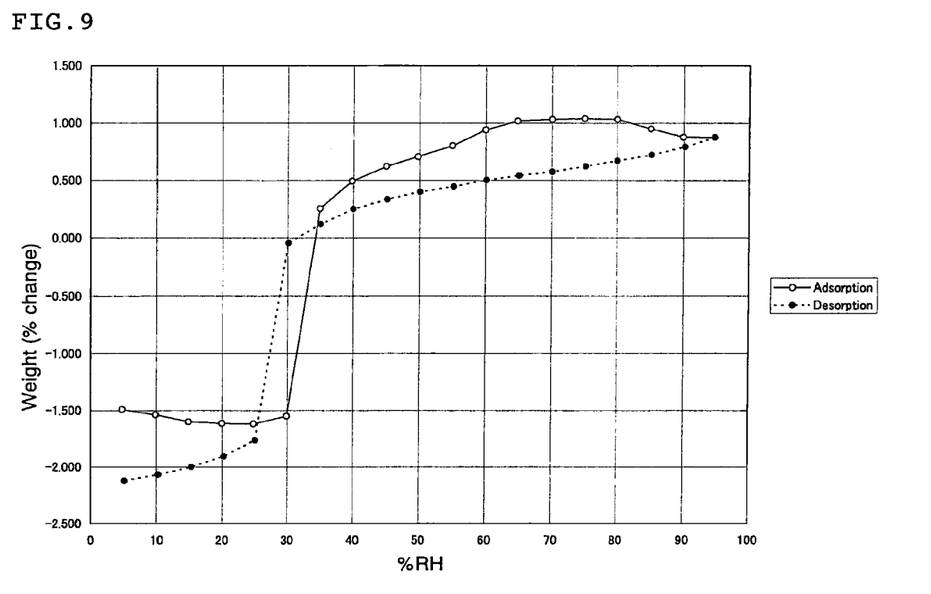
FIG. 9 is an absorption-desorption isotherm of (1S)-1,5-anhydro-1-[3-(1-benzothien-2-ylmethyl)-4-fluorophenyl]-D-glucitol (known compound A).

Weight change was measured by using of "VTI SGS-100" under the conditions of temperature=25° C., relative humidity range=5 to 95%, and relative humidity interval=5%. As a result, known compound A showed non-stoichiometric moisture absorption accompanied by physical change at low humidity. There was a sharp increase in weight particularly from relative humidity of 25 to 35% (see FIG. 9). Further, while known compound A gives moisture absorption curves slightly different from each other depending upon the particle size and crystal habit, there was a case that 3.2% of water was desorbed and absorbed at 25° C. at 5 to 95% RH.

Figure 10:
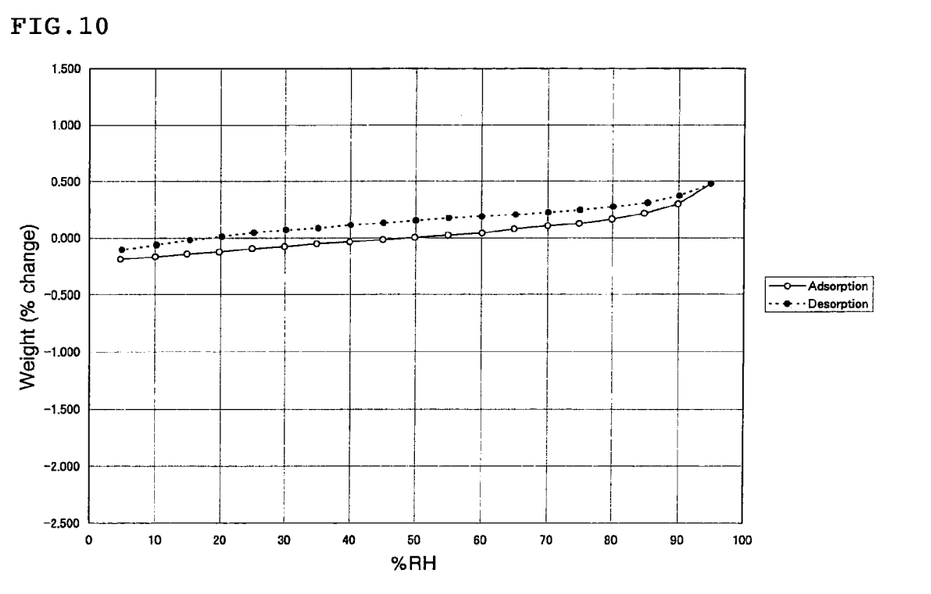
FIG. 10 is an absorption-desorption isotherm of a cocrystal (a cocrystal of the present invention) of (1S)-1,5-anhydro-1-[3-(1-benzothien-2-ylmethyl)-4-fluorophenyl]-D-glucitol and L-proline.

In contrast, the cocrystal of the present invention had moisture contents of 0.7% or less in a total relative humidity range of 5 to 95% and showed no moisture absorptivity (see FIG. 10). Also, the cocrystal was stable physically.

[Pharmacological Tests]

(Test 1) [Test for Confirming Effect of Inhibiting Activity of Human $Na^+$-Glucose Cotransporter (Human SGLT2)]

1) Preparation of Human SGLT2 Expression Vector

First, single-stranded cDNA was reversely transcribed from total RNA originating from human kidney (manufactured by BD Biosciences Clontech) using a Superscript II (manufactured by Invitrogen Corporation) and a random hexamer. Second, using the cDNA as a template, a DNA fragment encoding human SGLT2 (Wells R. G. et al., Am. J. Physiol., 1992, 263 (3) F459) was amplified by a PCR reaction using Pyrobest DNA polymerase (manufactured by Takara Bio Inc.) (A primer where a Hind III site and an EcoRI site were inserted into the 5' side and the 3' side of the DNA fragment, respectively, was used).

The amplified fragment was cloned into a pCR2.1-Topo vector using a Topo TA Cloning Kit (manufactured by Invitrogen Corporation), and the cloned vector was transfected into a competent cell of *Escherichia coli* JM109. Ampicillin-resistant clones were cultured in a LB medium containing ampicillin (100 mg/l). A plasmid was purified from the cultured *Escherichia coli* using the method of Hanahan (see Maniatis et al., "Molecular Cloning"). A DNA fragment for encoding a human SGLT2 was obtained by the Hind III/EcoRI digestion of the plasmid and ligated and cloned to the same site of the expression vector pcDNA3.1 (manufactured by Invitrogen Corporation) using a T4 DNA ligase (manufactured by Roche Diagnostics). The ligated clone was transfected into a competent cell of *Escherichia coli* JM109 in the same manner as described above and cultured in an LB medium containing ampicillin, and a human SGLT2 expression vector was obtained using the method of Hanahan.

2) Preparation of Human SGLT2 Expression Cells

The human SGLT2 expression vector was transfected into a CHO-K1 cells using Lipofectamine 2000 (manufactured by Invitrogen Corporation). The cell was cultured in a Ham's F12 medium (manufactured by Nissui Pharmaceutical Co., Ltd.) containing Penicillin (50 IU/mL, manufactured by Dainippon Pharmaceutical Co., Ltd.), streptomycin (50 μg/mL, manufactured by Dainippon Pharmaceutical Co., Ltd.), Geneticin (40 μg/mL, manufactured by Invitrogen Corporation), and 10% fetal bovine serum in the presence of 5% $CO_2$ at 37° C. for two weeks, and Geneticin-resistant clones were obtained. A cell which stably expresses the human SGLT2, which exhibits sodium-dependent intake of methyl-α-D-glucopyranoside, was obtained from among these clones (See the following paragraphs for the method for measuring the methyl-α-D-glucopyranoside intake).

3) Measurement of Inhibition of methyl-α-D-glucopyranoside Intake

After removing the medium of a CHO cell which stably express the human SGLT2, a pretreatment buffer solution (buffer solution of pH 7.4 containing choline chloride (140 mM), potassium chloride (2 mM), calcium chloride (1 mM), magnesium chloride (1 mM), 2-[4-(2-hydroxyethyl)-1-piperazinyl]ethanesulfonic acid (10 mM), and tris(hydroxymethyl)aminomethane (5 mM)) was added in the amount of 100 μl per well, and incubated at 37° C. for 20 minutes.

11 μl of methyl-α-D-(U-14C) glucopyranoside (manufactured by Amersham Pharmacia Biotech) was added to and mixed with 1,000 μl of a buffer solution for intake containing a cocrystal of the present invention (buffer solution of pH 7.4 containing sodium chloride (140 mM), potassium chloride (2 mM), calcium chloride (1 mM), magnesium chloride (1 mM), methyl-α-D-glucopyranoside (50 μM), 2-[4-(2-hydroxyethyl)-1-piperazinyl]ethanesulfonic acid (10 mM), and tris(hydroxymethyl)aminomethane (5 mM)) to prepare a buffer solution for intake. A buffer solution for intake without a test crystal was prepared for a control group. A buffer solution for basal intake without the crystal of the present invention containing choline chloride (140 mM) instead of sodium chloride for measuring the basal intake in the absence of sodium was prepared as well. A buffer solution for basic intake, which is used for measurement of basic intake in the absence of the cocrystal of the present invention and Na, containing 140 mM of choline chloride in place of sodium chloride was prepared as well.

After removing the pretreatment buffer solution, the buffer solution for intake was added (25 μl per well) and incubated at 37° C. for two hours. After removing the buffer solution for intake, a buffer solution for washing (buffer solution of pH 7.4 containing choline chloride (140 mM), potassium chloride (2 mM), calcium chloride (1 mM), magnesium chloride (1 mM), methyl-α-D-glucopyranoside (10 mM), 2-[4-(2-hydroxyethyl)-1-piperazinyl]ethanesulfonic acid (10 mM), and tris(hydroxymethyl)aminomethane (5 mM)) was added (200 μl per one well). The mixture was immediately removed. This washing operation was carried out once more. 0.5% lauryl sodium sulfate was added (25 μl per well) to solubilize the cells. 75 μl of Microscint 40 (manufactured by Packard, Corp.) was added to the solubilized cell, and the radiation activity was measured using a microscintillation counter Top-Count (manufactured by Packard, Corp.). The value obtained by subtracting the basal intake amount from the intake amount of the control group was defined as 100%. The concentration for 50% inhibition of the above value ($IC_{50}$ value) was calculated from a concentration-inhibition curve using the least-squares method. As a result, the $IC_{50}$ value of the cocrystal of the present invention was 5.8 nM.

(Test 2): [Test for Confirming Effect of Antihyperglycemic Action]

Non-fasted KK-$A^y$ mice (Clea Japan, Inc., male) were used as a test animal. The cocrystal of the present invention was suspended in an aqueous 0.5% methyl cellulose solution, in a concentration of 1 mg/10 mL. The body weight of each mouse was measured, and the suspension of the cocrystal of the present invention was forcibly administered orally in an amount of 10 mL/kg. Only the aqueous 0.5% methyl cellulose solution was administered to a control group. The number of mice per each group was 6. Blood samples were taken from the tail vein of each mouse right before administration and 1, 2, 4 and 8 hours after administration. Blood sugar value was measured using Glucose CII Test Wako (Wako Pure Chemical Industries, ltd.). From the blood sugar values of the cocrystal of the present invention-administered group at 0 to 8 hours were calculated an area under blood sugar value-time curve (AUC) according to the trapezoidal method; a ratio (%) of that area to the area of control group was determined; and it was taken as intensity of antihypoglycemic action. As a result, the cocrystal of the present invention showed a strong antihypoglycemic action.

From the results of the Test 1 and Test 2, the cocrystal os the present invention indicated the superior $Na^+$-glucose cotransporter-inhibiting action and the strong antihypoglycemic action. Therefore, it is expected that the cocrystal of the present invention can become a diabetes treating agent having the same or higher efficacy as or than those of conventional diabetes treating agents.

The invention claimed is:

1. A cocrystal of (1S)-1,5-anhydro-1-[3-(1-benzothien-2-ylmethyl)-4-fluorophenyl]-D-glucitol and L-proline having peaks at $2\theta(°)$ of 4.14, 8.98, 12.4, 16.5, 17.5, 18.7, 20.5 and 21.5 measured by X-ray powder diffraction.

2. The cocrystal according to claim 1, having an endothermic peak at 201 to 213° C. measured by differential scanning calorimetry (DSC analysis).

3. The cocrystal according to claim 2, wherein the molar ratio of (1S)-1,5-anhydro-1-[3-(1-benzothien-2-ylmethyl)-4-fluorophenyl]-D-glucitol and L-proline is 1:1.

4. A solid pharmaceutical composition comprising the cocrystal according to claim 1, and a pharmaceutically acceptable excipient.

5. A solid pharmaceutical composition comprising the cocrystal according to claim 1 in a dose effective to treat diabetes.

6. A method for treating diabetes comprising administering an effective therapeutic dose of the cocrystal according to claim 1 to patients in need thereof.

* * * * *